United States Patent
Gaspari et al.

(10) Patent No.: US 11,395,803 B2
(45) Date of Patent: *Jul. 26, 2022

(54) COMPOSITION FOR CONTROLLED RELEASE OF PHYSIOLOGICALLY ACTIVE SUBSTANCES AND PROCESS FOR ITS PREPARATION

(71) Applicant: BIOSCREEN TECHNOLOGIES S.R.L., Bertinoro (IT)

(72) Inventors: Enrico Gaspari, Meldola (IT); Flavio Farnedi, Cesena (IT); Devis Ungheri, Forli (IT); Arnaldo Valentini, Cesena (IT)

(73) Assignee: BIOSCREEN TECHNOLOGIES S.R.L., Bertinoro (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/489,051

(22) PCT Filed: Feb. 26, 2018

(86) PCT No.: PCT/IB2018/051190
§ 371 (c)(1),
(2) Date: Aug. 27, 2019

(87) PCT Pub. No.: WO2018/154532
PCT Pub. Date: Aug. 30, 2018

(65) Prior Publication Data
US 2020/0000733 A1    Jan. 2, 2020

(30) Foreign Application Priority Data
Feb. 27, 2017   (IT) .......................... 102017000021879

(51) Int. Cl.
*A61K 9/50*         (2006.01)
*A61K 31/14*        (2006.01)
*A61K 31/198*       (2006.01)
*A23K 40/30*        (2016.01)
*A23K 20/105*       (2016.01)
*A23K 50/10*        (2016.01)
*A23K 20/142*       (2016.01)

(52) U.S. Cl.
CPC .......... *A61K 9/5073* (2013.01); *A23K 20/105* (2016.05); *A23K 20/142* (2016.05); *A23K 40/30* (2016.05); *A23K 50/10* (2016.05); *A61K 9/5015* (2013.01); *A61K 9/5026* (2013.01); *A61K 9/5036* (2013.01); *A61K 31/14* (2013.01); *A61K 31/198* (2013.01)

(58) Field of Classification Search
None
See application file for complete search history.

(56) References Cited

U.S. PATENT DOCUMENTS

| | | | |
|---|---|---|---|
| 3,541,204 A * | 11/1970 | Sibbald et al. | ........ A23K 40/35 424/438 |
| 5,227,166 A | 7/1993 | Ueda et al. | |
| 5,405,628 A | 4/1995 | Ueda et al. | |
| 5,429,832 A | 7/1995 | Ueda et al. | |
| 2006/0067984 A1 * | 3/2006 | Cavassini | .............. A23K 40/30 424/438 |
| 2008/0044516 A1 | 2/2008 | Dollat et al. | |
| 2008/0119552 A1 | 5/2008 | Navarro | |
| 2011/0250286 A1 * | 10/2011 | Marcello | ................ A61K 47/12 424/498 |
| 2012/0093974 A1 | 4/2012 | Wright et al. | |
| 2016/0183558 A1 | 6/2016 | Nocek et al. | |
| 2016/0338948 A1 | 11/2016 | Adachi et al. | |

FOREIGN PATENT DOCUMENTS

| | | | |
|---|---|---|---|
| CN | 103168923 A | 6/2013 | |
| CN | 106455633 A | 2/2017 | |
| JP | S63317050 A | 12/1988 | |
| JP | H0523114 A | 2/1993 | |
| JP | H05192096 A | 8/1993 | |
| WO | WO-2006032958 A2 | 3/2006 | |
| WO | 2008/015203 A2 | 2/2008 | |
| WO | WO-2009045369 A1 | 4/2009 | |
| WO | WO-2009094421 A1 * | 7/2009 | ........... A23L 29/212 |
| WO | WO-2010122583 A2 | 10/2010 | |
| WO | 2011/140106 A1 | 5/2011 | |
| WO | WO-2011127236 A1 | 10/2011 | |
| WO | 2016/028286 A1 | 2/2016 | |
| WO | 2016028286 A1 | 2/2016 | |
| WO | WO-2018154532 A1 | 8/2018 | |

OTHER PUBLICATIONS

International Search Report and Written Opinion for International Application No. PCT/IB2018/051190, dated Jun. 7, 2018, European Patent Office, Netherlands, 12 pages.
Office Action for CN 201880025669 dated Mar. 31, 2021, 6 pages.
Office Action for related application MX/a/2019/010228 dated Aug. 11, 2021, 4 pages.
International Search Report and Written Opinion for PCT/IB2018/051189, dated Jun. 6, 2018, 11 pages.
First Office Action for CN 201880025668.8 dated Apr. 6, 2021, 19 pages.
Second Office Action for CN 201880025668.8 dated Dec. 1, 2021, 7 pages.
First Office Action for MX/a/2019/010229 dated Aug. 11, 2021, 10 pages.
Second Office Action in MX/a/2019/010229 dated Dec. 6, 2021, 10 pages.

(Continued)

*Primary Examiner* — Dominic Lazaro

(57) ABSTRACT

The present invention relates to a rumen-resistant composition in the form of microgranules, a process for its production and a feedstuff containing such composition.

21 Claims, No Drawings

(56) References Cited

OTHER PUBLICATIONS

Notice of Reasons for Refusal issued in related JP Application No. 2019567408, dated Feb. 22, 2022, 9 pages.
Jinzhuang, et al., "Research Progress of Rumen-passing Amino Acids" Feed Industry, 2006, 27(17):38-40.

\* cited by examiner

COMPOSITION FOR CONTROLLED RELEASE OF PHYSIOLOGICALLY ACTIVE SUBSTANCES AND PROCESS FOR ITS PREPARATION

The present invention relates to a controlled release composition of physiologically active substances for zootechnical use. In particular, the subject of the present invention is a composition comprising microgranules capable of releasing in a controlled way the physiologically active substances they contain, a process for the production of such microgranules and their use in zootechnics.

It is known that physiologically active substances can be used to supplement or add additives to the diet of farm animals, in order to improve their health conditions, increase their productive longevity and increase their zootechnical performance.

The physiologically active substances thus used include for example amino acids, vitamins, enzymes, nutrients such as proteins and carbohydrates, probiotic microorganisms, prebiotic foods, mineral salts, choline and its derivatives.

Some of the above-mentioned physiologically active substances are already normally present in feedstuff used for animal feeding. However, sometimes the intake of these active substances, present in the diet, may be insufficient or inadequate to deal with deficiencies or situations of high productivity.

These physiologically active substances, having nutritive properties, are administered by mouth to the animals through formulated products (premixtures or complementary feedstuff) in which said active substances are "diluted" by mixing with a medium; the resulting product is then added to the feedstuff.

However, the active substances and feedstuff containing these active substances undergo an enzymatic chemical degradation in the first section of the animal digestive tract. In the case of ruminants (in which, before reaching the intestine, the food must pass through three forestomachs plus the glandular stomach) the degradation can be particularly intense owing to two main concomitant factors: a long transit time of the feedstuff in the forestomachs (especially in the rumen) and the presence of the microbial flora that performs a degrading action on most of the molecules passing through the rumen.

The action of ruminal microorganisms chemically alters some active substances, such as choline, transforming them into substances with a lower nutritional value or with a significantly reduced biological activity compared to the initial compound.

Moreover, the said active substances undergo further degradation during the preparation of the formulations, especially during the mixing, packaging and storage phases, as well as during the compaction treatments, due to the application of heat and/or pressure and/or steam.

In an attempt to provide solutions to release physiologically active substances in a rumen-protected form, i.e. protected from degradation in the ruminal environment, allowing the release of substances at a time following the rumen, several products have been proposed.

U.S. Pat. No. 3,959,493 describes a rumen by-pass product for oral administration to ruminants. Said product is in form of particles comprising an amount of a biologically active substance lower than 40% and a protective substance resistant to the ruminal environment and present in an amount of at least 60% by weight with respect to the weight of the particle. This protective substance is digestible in the ruminant lower digestive tract and consists of saturated and unsaturated aliphatic fatty acids, comprising from 14 to 22 carbon atoms.

U.S. Pat. No. 6,797,291 describes a method for stabilizing a hygroscopic ingredient in a wet composition, comprising the encapsulation of said hygroscopic ingredient in a lipid coating consisting for example of waxes, fatty acids, alcohols or esters derived from fatty acids, sterols, phospholipids and hydrogenated oils.

However, the products described in these documents are characterized by poor preservation stability, low concentrations of active substances and reduced post-ruminal digestibility.

US2011/250286 describes compositions in the form of microparticles or granules for the controlled release of physiologically active substances arranged in cores which are coated by a layer of fatty acids and a second layer of fatty acids and glycerides.

EP2274990 describes a method for producing a complementary ruminant feedstuff composition comprising the preparation of a mixture of a protective agent selected from animal or vegetal oils having a melting point of between 50° C. and 90° C.; lecithin and an amino acid; and the dripping of this mixture into water in order to make it solid.

U.S. Pat. No. 4,876,097 describes a composition comprising a coating with controlled hydrophilia and sensitive to pH variations comprising chemically modified cellulose.

U.S. Pat. No. 8,906,407 describes a composition comprising an ethyl-cellulose based coating.

However, the herein described compositions are poorly stable during the production of the feedstuff or the supplements, where they are mixed with other ingredients which can remove their coating layer, thus making the product ineffective.

Another drawback of such known compositions is that mixing with an acidic ingredient, e.g. containing corn silage, may cause the coating to react even before the composition is administered to the animals.

EP1791532 describes a microgranule composition suitable for the controlled release of physiologically active substances in the ruminant post-ruminal tract, comprising a core and two coating layers. The first coating layer comprises a first hydrophobic substance selected from fats, fatty acids, hydrogenated oils, mono- and di-glycerides of fatty acids, esters of fatty acids, fatty alcohols, with chains of 12 to 22 carbon atoms and a melting point from 40° C. to 74° C. The second coating layer comprises a second hydrophobic substance selected from microcrystalline waxes, paraffin waxes, vegetal and synthetic waxes with a melting point between 80° C. and 100° C.

The composition described in this document guarantees a high degree of ruminal crossing (bypass), a good in vivo efficacy, excellent chemical, thermal and mechanical resistance, and high mixability and pelletability properties.

However, it is desirable to further improve the post-ruminal digestibility of the substances included in a microgranule composition, enhancing the total bioavailability of these substances.

The object of the present invention is thus to provide a composition for zootechnical use capable of releasing the substances contained therein in a controlled way, in the animal assimilation tracts namely from the abomasum to the small intestine, which does not have the drawbacks of the compositions according to the state of the art.

Said object is achieved with a rumen-resistant composition, the main features of which are specified in the first claim, a process for the preparation of such composition, the characteristics of which are specified in the respective independent claim, a feedstuff premixture comprising said composition, the characteristics of which are specified in the respective independent claim regarding a premixture, and a feedstuff composition comprising said premixture, the characteristics of which are specified in the independent claim. Other features of the composition according to the present invention are specified in the remaining dependent claims.

An advantage of the composition according to the present invention consists in the fact that it releases the physiologically active substances in the post-ruminal zone in a controlled way, achieving an improved total bioavailability of these substances.

In the context of the present invention, the term "ruminal by-pass" indicates the percentage amount by weight of substance reaching the animal post-ruminal area, namely the stomach and the intestine, with respect to the total amount by weight of the orally administered substance.

Whereas, the term "post-ruminal digestibility" of a substance means the percentage amount by weight of substance that is freed from the coating exclusively in the post-ruminal tract, dissolving and so making it digestible or absorbable, with respect to the total amount by weight of the orally administered substance.

The term "total bioavailability" of a substance is used to indicate the percentage amount by weight of the substance that reaches the animal systemic circulation in a biologically active form, with respect to the total amount by weight of the orally administered substance.

Thus, a total bioavailability of a substance is defined by the combination of the two values of ruminal bypass and post-ruminal digestibility.

In fact, using methodologies known in the pharmaceutical industry, it has been established that the physiologically active substances administered by means of the compositions according to the present invention are bioavailable, in a non-degraded form, in percentages higher than those of the compositions according to the state of the art.

Furthermore, the composition for zootechnical use according to the present invention has controlled chemical and physical properties and is resistant to mechanical-structural degradation.

These and other advantages of the rumen-resistant composition and its production process according to the present invention will be evident to those skilled in the art from the following detailed description of some embodiments.

The rumen-resistant composition according to the present invention is in form of microgranules, wherein each microgranule comprises a core and one or more coating layers.

Said core contains one or more physiologically active ingredients or substances, generally in solid form, and a matrix.

Any substance that is to be administered to the animals in non-degraded form can in principle be contained in the core of the microgranules of the composition according to the present invention. As is known, the physiologically active substances contained in the core of the microgranules can be chosen from the group consisting of amino acids, vitamins, enzymes, nutrients such as proteins and carbohydrates, probiotic microorganisms, prebiotic foods, mineral salts, mixtures of acids such as lactic, fumaric, sorbic, formic, citric, malic, acetic, butyric and propionic acid, choline and choline derivatives such as choline chloride, choline bitartrate, citrate dehydrogenated choline, choline bicarbonate, choline sulfate and choline hydroxide. These physiologically active substances can be used alone or mixed together in different weight ratios.

In a preferred embodiment, the physiologically active substance is selected from: methionine, choline, choline chloride, lysine, lysine hydro-chloride, lysine sulfate, vitamin C and its derivatives, vitamin A and its derivatives, vitamin E and its derivatives, vitamin D3 and its derivatives, vitamin B1 and its derivatives, vitamin B2 and its derivatives, vitamin B6 and its derivatives, vitamin B12, vitamin H, vitamin PP and its derivatives and a mixture of acids comprising lactic, fumaric, sorbic, formic, citric, malic, acetic, butyric and propionic acid.

Said matrix, mixed with the physiologically active substance to obtain a uniform heterogeneous mixture, comprises at least one substance selected from substances having a binding action and inert substances.

The substances with binding action, used in the matrix, are typically non-toxic substances of vegetal or synthetic origin such as rubber, cellulose and its derivatives, amides and derivatives, waxes and derivatives and fats and derivatives.

Advantageously, vegetal waxes such as carnauba wax, rice wax, microcrystalline waxes, fats and their derivatives are used. In a preferred embodiment, the binder is a combination of rice wax and microcrystalline wax in a weight ratio of 1:3 to 3:1; advantageously 1:1.

In an alternative embodiment, the binder is a combination of rice wax and fatty acid derivatives in a weight ratio of 1:3 to 3:1; advantageously 1:1. As derivatives of fatty acids, salts such as zinc, magnesium or calcium salt can be used.

The inert ingredients, used in the formation of the matrix, are sliding substances and generally belong to the category of silicates, in particular hydrophobic silicates such as colloidal silica, synthetic amorphous silica, precipitated silica, sodium aluminum silicates, calcium silicate, talc, kaolin, hydrophobic synthetic zeolites.

The total amount by weight of binding substances and inert substances in the core of the composition according to the present invention is preferably between 1% and 70% of the total weight of the core. More preferably, the total amount of substances having a binding and inert action is between 10% and 30% by weight, and even more preferably it is between 12% and 17% by weight of the total core weight.

According to the invention, the core of the granules can comprise at least one disintegrant agent. This disintegrant agent is present in the core of the composition according to the present invention in an amount by weight preferably comprised between 1% and 20% with respect to the total weight of the core. More preferably, the amount by weight of disgregant substances is comprised between 1.5% and 6% by weight and even more preferably between 2% and 5% of the total weight of the core.

In the context of the present invention, the term disintegrant agent indicates a substance capable of modifying its own state or action in presence of a post-ruminal aqueous environment and causing a rapid disintegration of the core once it has interacted with a aqueous environment or it is a substance that is capable of recalling water in the core or favouring a disintegration of the core. The active ingredients may thus be provided with an improved post-ruminal digestibility thanks to the action of the disintegrant agents. In fact, it has surprisingly been found that said disintegrant agents improve the release of physiologically active substances once the composition comes into contact with the post-ruminal environment.

Disintegrant substances suitable for this purpose are emulsifiers, thickeners, effervescent mixtures, polysaccharides and methacrylate polymers.

Preferably, the disintegrant compounds which can be used in the core of the compositions according to the present invention, and in the amounts identified above, are selected from the following group: amides in dry form; vegetal lecithins, such as soy lecithin or sunflower lecithin, or a combination thereof ethoxylated oils; mono- and diglycerides of fatty acids; agar-agar or gum arabic in dry form; effervescent mixtures, capable of developing carbon dioxide, such as that formed of at least one bicarbonate of an alkali metal or of ammonium and at least one polycarboxylic acid such as citric or tartaric acid, such as a combination of citric acid and sodium bicarbonate; cellulose in dry form and/or not previously wetted; and methacrylate polymers, or a combination thereof. With respect to cellulose in dry form, it should be noted that, when it comes into contact with the aqueous post-ruminal environment, it tends to absorb moisture, swell and therefore facilitate the disintegration of the core containing the active ingredients.

The microgranules of the composition according to the present invention comprise at least two core coating layers having a different composition.

Preferably, each layer comprises a pollutant, in a different amount between the first and second layers. In other words, all the layers can contain pollutants differently both in terms of percentage and quality.

The choice of pollutants, in percentage and/or type, may depend on the core type and characteristics, for example due to the presence of disintegrants, or a greater solubility of the active ingredient. In the case of a core having disintegrating agents and an active ingredient with greater solubility, the core may be coated with less polluted layers than a less easily disintegrating granule. For example, choline chloride and lysine HCl have a much higher solubility than methionine or nicotinic acid and consequently, different components should be used to obtain products with optimal performances.

According to the invention, the polluting substance, or a substance altering the characteristics that this coating layer would have in its absence, is chosen from the group consisting of emulsifying substances such as vegetal lecithins, ethoxylated oils and alginates and/or from the group of fatty acids and/or from the group of methacrylate copolymers. As emulsifying substances in the at least two coating layers, soy or sunflower lecithin, ethoxylated castor oil, alkali metal alginates and magnesium can advantageously be used. As polluting fatty acids in the at least two coating layers, palmitic acid, oleic acid, acid linoleic, linolenic acid, stearic acid or a combination thereof can advantageously be used. As polluting copolymer in the at least two coating layers, PMMA (polymethyl methacrylate) can advantageously be used. As polluting substance in the at least two coating layers, different combinations of emulsifying substances and/or polluting fatty acids and/or polluting methacrylate copolymer can advantageously be used.

According to a preferred embodiment of the invention, each coating layer includes a quantity of emulsifying substance comprised between 0.01% and 15% by weight of the weight of the coating layer. More preferably, each coating layer includes a quantity of emulsifying substance comprised between 0.1% and 6% by weight of the weight of the coating layer.

According to a preferred embodiment of the invention, each coating layer includes a quantity of polluting fatty acids comprised between 1% e 40% by weight of the weight of the coating layer. More preferably, each coating layer includes a quantity of polluting fatty acids comprised between 10% and 35% by weight of the weight of the coating layer.

In each microgranule the total weight of the coating layers is between 10% and 50% of the weight of the microgranule, more preferably the total weight of the coating layers is between 15% and 40% of the weight of the microgranule.

The fact that the two coatings have a different composition allows the post-ruminal permeability of the coating layers to be modulated, and therefore they have a double function of protection within the rumen and of gradual release in the successive digestive tracts. In other words, the presence of two different coating layers allows the action of pollutants in the coatings to be modulated in order to achieve an optimum compromise between ruminal resistance and post-ruminal digestibility, and, consequently, bioavailability.

In even other words, it is possible to modulate the permeability of the overall coating layer by applying alternating layers having a different composition. In this way layers that are more permeable/digestible are alternated with less permeable/digestible layers, always with a view to "exploiting" the 8 hours presence in the rumen as "activation" of the product which, hour after hour, undergoes increasing degradation until it weakens and becomes accessible, once it has passed the ruminal tract for physiological reasons, since, as known by the experts in the field, the transit time in the rumen for this kind of product is estimated at 6-8 h.

Preferably, the two coating layers consist of an external layer and a more inner layer. The external coating comprises, for example, at least a first layer composed of a substance forming a water-repellent film which is stable at the rumen environmental conditions, for example, for at least 8 hours, and at least one second protective layer for protection against mechanical abrasion and impact, for example resistant to temperatures of between 75° and 90° C.

Even more particularly, in a preferred form, the pollutant of each layer includes palmitic acid, oleic acid, linoleic acid, linolenic acid, stearic acid, or a combination thereof. In particular the pollutant includes single fatty acids, which are much more digestible than hydrogenated waxes and triglycerides used as coating layers, therefore tending to be more easily digested and consequently to create, over time, micro-channels (lesions) in the coating structure thus allowing water to enter gradually.

Preferably, emulsifying substances of one or each layer include lecithin of soy or sunflower, which have the function of letting water slowly enter the coating layers.

In one embodiment, emulsifying substances of one or each layer include ethoxylated castor oil.

In one embodiment, emulsifying substances of one or each layer include sodium or magnesium alginate. This substance is more digestible than waxes and triglycerides, and tends to be more easily digested and, consequently, over time, to create micro-channels (lesions) in the structure of the coating, allowing water to enter gradually.

In one embodiment, polluting fatty acids of one or each layer include palmitic acid, which tends to be easily digestible and, consequently, over time, tends to create micro-channels (lesions) in the structure of the coating, allowing water to enter gradually.

In one embodiment, polluting fatty acids of one or each layer include oleic acid.

In one embodiment, polluting fatty acids of one or each layer include linoleic acid.

In one embodiment, polluting fatty acids of one or each layer include linolenic acid.

In one embodiment, polluting fatty acids of one or each layer include stearic acid.

In one embodiment, polluting fatty acids of one or each layer include a combination of the afore-mentioned fatty acids.

In one embodiment, pollutants include polymethyl methacrylate (PMMA): pH-dependent polymer which is solubilised at acidic (stomacal) pH, while it remains solid between a weakly acid pH (5) and weakly basic pH (8): range comprising the pH values found in the rumen of healthy animals. Consequently, if it is wetted by a stomach solution it dissolves, but it does not dissolve if wetted by a rumen solution.

According to an embodiment of the present invention, microgranules of the composition can be made in which said first and second layer are repeatedly deposited so as to form a covering comprising three, four or more coating layers.

Moreover, the microgranules of the composition according to the present invention can comprise further coating layers, having a composition different from that indicated for said first and second layer.

In fact, it has been found that this repeated and alternate arrangement of the first and second layer, and/or the application of further layers with different formulations, allows the water permeability of the microgranule to be modulated so that it remains waterproof for a period of time necessary for it to pass beyond the ruminal tract. This period of time may vary according to the size of the microgranules, their specific weight and buoyancy, i.e. their placement within the layers in which the rumen content is subdivided, but is normally within the range of 6-8 hours. Instead, the time which microgranules spend within the area of the post-ruminal digestive tracts, can be generally quantified in a further 24 hours.

The microgranules of the composition according to the present invention are advantageously impermeable for the first 10 to 12 hours of immersion in the digestive environment of ruminants, and subsequently they become more and more permeable to the external environment.

Said first coating layer of the core consists of one or more physiologically acceptable substances having hydrophobic properties.

The hydrophobic substances forming said first layer are selected from the group consisting of: fats, fatty acids, hydrogenated oils, mono and diglycerides of fatty acids, salts of fatty acids such as zinc, magnesium or calcium stearate, esters of fatty acids and fatty alcohols and their mixtures.

These hydrophobic substances are preferably selected from: hydrogenated soybean oil, hydrogenated rapeseed oil, hydrogenated cotton oil, hydrogenated palm oil, hydrogenated linseed oil, sodium glyceryl mono-, di-, tri-stearate, calcium stearate, magnesium stearate, zinc stearate, stearyl alcohol, cetylstearyl alcohol.

Advantageously, the hydrophobic substances are selected from hydrogenated palm oil and/or hydrogenated soy oil.

A second layer, arranged on the outside of said first layer, comprises at least one second physiologically acceptable substance, or a mixture of substances, having hydrophobic properties. Said second hydrophobic substance or mixture of substances is resistant to mechanical stress and maintains its chemical-physical properties unchanged up to a temperature of 80° C.

Said second hydrophobic substance included in said second layer is selected from the group consisting of: microcrystalline waxes, paraffin waxes, vegetal waxes and edible synthetic waxes. Advantageously, said second hydrophobic substance is selected from the group consisting of rice wax, carnauba wax and/or microcrystalline waxes.

With respect to the core disintegrant agents, they can also include only soy lecithin, which, as emulsifier, has the function of recalling water within the core and enhances the contact of the active ingredients with water, favouring the solubilization thereof.

Alternatively, disintegrant agents include a combination of citric acid and sodium bicarbonate: they are an effervescent mixture having the function of swelling the core. The respective percentages of citric acid and sodium bicarbonate in the mixture are in the range 30%-70% of former and 70%-30% of the latter and more preferably 50%-50%.

In another embodiment, disintegrant agents include a combination of soy lecithin and citric acid/sodium bicarbonate: the two functions mentioned above are combined, i.e. the lecithin draws water towards the inside, favouring the solubilization and at the same time favouring the effervescent acid/base reaction.

The respective percentages of soya lecithin, citric acid and sodium bicarbonate in the mixture are comprised, respectively, in the ranges 30%-60%, 20%-40% and 20%-40%, and more preferably 40% (lecithin), 30% (citric acid) and 30% (sodium bicarbonate).

Preferably, disintegrant agents include only sunflower lecithin.

Preferably, disintegrant agents include carboxymethyl cellulose (CMC): inserted dry—not previously wetted—since. if it were wetted during the core production it would be unable to perform the disintegrating function required in the post-ruminal phase.

Preferably, disintegrant agents include dry inserted corn starch having a similar function to CMC.

Preferably, disintegrant agents include ethoxylated castor oil, which has a function similar to soy lecithin.

Preferably, disintegrant agents include palmitic acid, oleic acid, linoleic acid, linolenic acid and/or stearic acid, or a combination thereof; that is to say they are single fatty acids, which are digestible and tend to be more easily digested than the binders used in the core and, consequently, tend to make more digestible the core containing them.

Preferably, disintegrant agents include agar agar-gum arabic, which are inserted in dry form so as to make them swell once wet. Moreover, in the same way as for the above mentioned fatty acids, they are much more digestible than rice wax and classic vegetal waxes that are used as extrusion binders, so they tend to be more easily digested and, consequently, to make more digestible the core containing them.

Preferably, disintegrant agents include polymethyl methacrylate (PMMA): pH-dependent polymer which is solubilised with acidic (stomac) pH, while it remains solid between a weakly acid pH (5) and weakly basic pH (8): this range comprising the pH values found in the rumen of healthy animals. Consequently, PMMA, if wetted by a stomach solution, dissolves, but it does not dissolve if wetted by a ruminal solution.

In a preferred form of the present disclosure, the rumen-resistant composition according to the present disclosure includes any combination of disintegrating agents in the core, as defined above and pollutants, as defined above in the coating layers. It follows that this combination allows improved post-ruminal digestibility to be obtained compared to products without it, said improved post-ruminal digestibility being conferred to the active ingredients owing to the synergistic action between disintegrating agents in the core and polluting agents in the coating layers.

The present invention also relates to a process for the preparation of the microgranule composition described above.

The process comprises a step of mixing the substances forming the core, i.e. the physiologically active substances, the matrix substances and disintegrant substances, which is carried out in a container equipped with mixing, cutting, heating and cooling. Mixing is carried out until a homogeneous mixture is obtained.

In case of a physiologically active substance with a high microgranulometry, a preliminary micronization treatment may be necessary. As highlighted above, the core may comprise one or more physiologically active substances and the resulting mixture must be solid enough for the cores to remain intact during subsequent processing steps, particularly during the coating operations.

The process for preparing the composition of microgranules according to the present invention comprises a subsequent step of extrusion of the mixture thus obtained.

The mixture obtained is extruded into an extruder so as to obtain microgranules of the required shape and size.

The extruder, known to those skilled in the art, is advantageously a bi-screw extruder provided with feeding and mixing, and sectors provided with heating and cooling means that allow application of a temperature gradient based on the treatment carried out. The head of the extruder is equipped with a heatable and/or coolable die and provided with a plurality of outlet holes with a predetermined diameter.

Outside the die the composition is subjected to cutting with a cutter with variable speed that allows the length of the microgranule core to be adjusted.

The core thus obtained is subjected to cooling and sieving to remove powders and waste matter of undesirable dimensions.

At this point the cores can be subjected to the coating step.

In an alternative embodiment of the present invention, before the coating step, the core obtained after cooling and sieving is subjected to a spheronization operation or to another treatment for modifying its shape. The spheronization operation can be carried out with a rotating disk spheronizer, blowing in air and adjuvants such as softeners, thickeners and aggregating agents.

The spheroidal shape has the advantage of greater compactness, smoothness, coatibility and mixability, compared to the cylindrical shape.

Indeed, according to the present invention, it has been found that the spheroidal shape allows a better uniformity of the coating to be obtained, this allowing a more effective protective action of the coating for the same thickness of the applied protective layers.

The cores of the rumen-resistant composition according to the present invention can alternatively be obtained through the following techniques:
- dry and/or wet composition, wherein the physiological active substances are mixed with the matrix substances until forming irregular microgranules;
- compression together with the matrix substances;
- dripping: wherein the physiological active substance are dispersed in waxes or melted waxes forming a mixture that is dripped in a cooling liquid;
- spray-cooling: wherein the physiological active substance are dispersed in the melted matrix and sprayed in a cooling tower;
- coacervation: wherein the physiological active substance are melted in a solution with the matrix and then injected in a solution of water and hardener (for example $CaCl_2$). The sphere thus obtained is then dried and potentially coated.

According to an embodiment of the invention, the core of the microgranules of the rumen-resistant composition has a cylindrical shape, the height of which is comprised between 0.5 mm and 2 mm. According to an alternative embodiment, the core of the microgranules of the rumen-resistant composition has a substantially spheroidal shape, the diameter of which is comprised between 0.5 mm and 2 mm.

Subsequently, the cores thus obtained are subjected to a coating step. The coating layers can be applied in a pan, by a coating technique known to those skilled in the art. Alternatively, fluid bed coating techniques can be used, for example top spray fluid bed, bottom spray fluid bed or tangential spray fluid bed; or spray techniques with a single component or a mixture of components, or the dry-coating technique.

Further advantages and characteristics according to the present invention will be clear to those skilled in the art from the following detailed and non-limiting description of an embodiment thereof with reference to the following examples.

EXAMPLES

For the following examples, the following analysis and inspection tools were used:
Sieves, arranged at the end of each single production step, for the microgranule dimension line check;
Microscope for visual checks;
Melting point gauge for thermal resistance check;
Penetrometer for hardness and mechanical resistance check;
Automatic titrator or HPLC for the quantitative determination of the active ingredients (concentration);
Pharmaceutical dissolver for determining the degree of ruminal bypass. The experimental conditions of use were 39° C., 15 rpm, 8 hours presence in the solution with "ruminal" pH of about 6.8.
Daisy$^{II}$ ANKOM: commercially available laboratory artificial rumen, for determining the degree of ruminal bypass. The experimental conditions of use were 39° C., 8 hours presence in ruminal conditions, buffer solution at "ruminal" pH with insertion of "ruminal inoculum" and re-creation of ruminal anaerobiosis according to a university procedure known to those skilled in the art. The pH normally tested in the quality control phase is 6.8.
Pharmaceutical dissolver for determining the degree of post-ruminal digestibility. The experimental conditions of use followed the procedure known to experts in the field as "Boisen Test" and, in particular, they were:
39° C., 30 rpm, 2 h, buffer solution with "gastric" pH (2.0)+pepsin inoculum.
39° C., 30 rpm, 4 h, buffer solution with "intestinal" pH (6.8)+pancreatine inoculum.
39° C., 30 rpm, 18 h, buffer solution with "intestinal" pH (6.8)+lipase and bile extract inoculum.

Example 1—Preparation of Microgranules Containing Choline Chloride

Example 1.1

425 kg of choline chlorine with a purity of 99% were mixed with 10 kg of spray rice wax, 15 kg of zinc stearate, 10 kg of soy lecithin and 40 kg of silica. The mixture was extruded using an extruder with sectors at different temperature gradients according to the following program:

| Sector 1 | Sector 2 | Sector 3 | Sector 4 | Sector 5 | Sector 6 |
|---|---|---|---|---|---|
| 85° C. | 85° C. | 50° C. | 50° C. | 45° C. | 65° C. |

The cores thus obtained had a concentration of 85% in choline chloride. The cores were subsequently subjected to coating in a pan.

A first coating layer was formed, coating 400 kg of microgranules with 120 kg of a coating mixture comprising:
65% by weight of hydrogenated palm oil;
32% by weight of palmitic acid;
3% by weight of soy lecithin.

A second coating layer was then formed, coating the microgranules coated by the first layer with 40 kg of a coating mixture comprising:
50% by weight of hydrogenated palm oil;
50% by weight of rice wax.

All the above indicated percentages are percentages by weight based on the total weight of the covering layer.

The microgranules thus obtained had a concentration of 60% by weight of choline chloride with respect to the total weight of the microgranules.

Then the microgranules were subjected to an evaluation of the degree of ruminal by-pass, post-ruminal digestibility and total bioavailability using the Boisen method. For a complete description of the Boisen method, reference is made to the publication S. Boisen, J. A. Fernàndez "*Prediction of total tract digestibility of energy feedstuffs and FIG. diets by in vitro analyses*" Animal Feed Science Technology 68, 277-286, 1997.

The in vitro results are highlighted in Table 1.

TABLE 1

| Sample | Content (%) | Degree of ruminal bypass (*) | Digestibility () | Bioavailability () |
|---|---|---|---|---|
| 1 | 59.4 | 80.3 | 89.3 | 71.7 |

Example 1.2

425 kg of choline chlorine with a purity of 99% were mixed with 10 kg of spray rice wax, 15 kg of zinc stearate, 10 kg of soy lecithin, 5 kg of citric acid, 5 kg of sodium bicarbonate and 30 kg of silica. The mixture was extruded using an extruder with sectors at different temperature gradients according to the following program:

| Sector 1 | Sector 2 | Sector 3 | Sector 4 | Sector 5 | Sector 6 |
|---|---|---|---|---|---|
| 70° C. | 75° C. | 80° C. | 80° C. | 80° C. | 85° C. |

The cores thus obtained had a concentration of 85% in choline chloride. The cores were subsequently subjected to coating in a pan.

A first coating layer was formed, coating 400 kg of microgranules with 100 kg of a coating mixture comprising:
75% by weight of hydrogenated palm oil;
23% by weight of palmitic acid;
2% by weight of ethoxylated castor oil.

A second coating layer was then formed, coating the microgranules coated by the first layer with 60 kg of a coating mixture comprising:
50% by weight of hydrogenated rapeseed oil;
45% by weight of carnauba wax;
5% by weight of polymethyl methacrylate.

All the above indicated percentages are percentages by weight based on the total weight of the covering layer.

The microgranules thus obtained had a concentration of 60% by weight of choline chloride with respect to the total weight of the microgranules.

Then the microgranules were subjected to an evaluation of the degree of ruminal by-pass, post-ruminal digestibility and total bioavailability using the Boisen method. For a complete description of the Boisen method, reference is made to the publication S. Boisen, J. A. Fernàndez "*Prediction of total tract digestibility of energy feedstuffs and FIG. diets by in vitro analyses*" Animal Feed Science Technology 68, 277-286, 1997.

The in vitro results are highlighted in Table 2.

TABLE 2

| Sample | Content (%) | Degree of ruminal bypass (*) | Digestibility () | Bioavailability () |
|---|---|---|---|---|
| 2 | 59.7 | 78.2 | 92 | 71.9 |

Example 1.3

The extruded cores obtained with the procedure of Example 1.2 were spheronized with the use of an aqueous 75% choline chloride solution as an adjuvant for spheronization and subsequently they were coated in a pan.

A first coating layer was formed, coating 400 kg of spheroidal microgranules with 125 kg of a coating mixture comprising:
72% by weight of hydrogenated palm oil;
25% by weight of palmitic acid;
3% by weight of ethoxylated castor oil.

A second coating layer was then formed, coating the microgranules coated by the first layer with 20 kg of a coating mixture comprising:
50% by weight of hydrogenated palm oil;
50% by weight of rice wax.

Finally, a third coating layer of 20 kg containing 100% of polymethyl methacrylate was formed.

All the above indicated percentages are percentages by weight based on the total weight of the covering layer.

The microgranules thus obtained had a concentration of 60% by weight of choline chloride with respect to the total weight of the microgranules.

The in vitro results are highlighted in Table 3.

TABLE 3

| Sample | Content (%) | Degree of ruminal bypass (*) | Digestibility () | Bioavailability () |
|---|---|---|---|---|
| 3 | 61.4 | 86.4 | 85.0 | 73.4 |

Example 2—Preparation of Microgranules Containing Lysine HCl

Example 2.1

400 kg of micronized lysine hydrochloride were mixed with 60 kg of granulated rice wax, 48 kg of powdered powder, and 12 kg of soy lecithin. The mixture was extruded using an extruder with sectors at different temperature gradients according to the following program:

| Sector 1 | Sector 2 | Sector 3 | Sector 4 | Sector 5 | Sector 6 |
| --- | --- | --- | --- | --- | --- |
| 85° C. | 65° C. | 50° C. | 50° C. | 50° C. | 50° C. |

The cores thus obtained had a concentration of 75% in lysine hydrochloride. The cores were subsequently subjected to coating in a pan.

A first coating layer was formed, coating 350 kg of microgranules with 100 kg of a coating mixture comprising:
  95% by weight of hydrogenated palm oil;
  5% by weight of sunflower lecithin.

A second coating layer was then formed, coating the microgranules coated by the first layer with 75 kg of a coating mixture comprising:
  50% by weight of hydrogenated rapeseed oil;
  48% by weight of carnauba wax;
  2% by weight of sunflower lecithin.

All the above indicated percentages are percentages by weight based on the total weight of the covering layer.

The microgranules thus obtained had a concentration of 50% by weight of lysine hydrochloride with respect to the total weight of the microgranules.

Then the microgranules were subjected to an evaluation of the degree of ruminal by-pass, post-ruminal digestibility and total bioavailability using the Boisen method. For a complete description of the Boisen method, reference is made to the publication S. Boisen, J. A. Fernàndez "Prediction of total tract digestibility of energy feedstuffs and FIG. diets by in vitro analyses" Animal Feed Science Technology 68, 277-286, 1997. The in vitro results are highlighted in Table 4.

TABLE 4

| Sample | Content (%) | Degree of ruminal bypass (*) | Digestibility () | Bioavailability () |
| --- | --- | --- | --- | --- |
| 4 | 50.2 | 73.4 | 86 | 63.1 |

Example 2.2

324 kg of micronized lysine hydrochloride were mixed with 64 kg of rice wax spray and 12 kg of soy lecithin. The mixture was extruded using an extruder with sectors at different temperature gradients according to the following program:

| Sector 1 | Sector 2 | Sector 3 | Sector 4 | Sector 5 | Sector 6 |
| --- | --- | --- | --- | --- | --- |
| 85° C. | 85° C. | 80° C. | 80° C. | 80° C. | 80° C. |

The cores thus obtained had a concentration of 80% in lysine hydrochloride. The cores were spheronized, using a 50% lysine hydrochloride solution in water as a spheronization adjuvant, and subsequently subjected to coating in a pan.

A first coating layer was formed, coating 350 kg of microgranules with 90 kg of a coating mixture comprising:
  75% by weight of hydrogenated palm oil;
  23% by weight of palmitic acid;
  2% by weight of ethoxylated castor oil.

A second coating layer was then formed, coating the microgranules coated by the first layer with 50 kg of a coating mixture comprising:
  48% by weight of hydrogenated rapeseed oil;
  52% by weight of rice wax;
  2% by weight of sunflower lecithin.

A third coating layer was then formed, coating the microgranules coated by the second layer with 40 kg of a coating mixture identical to that of the first layer.

A fourth coating layer was then formed, coating the microgranules coated by the third layer with 30 kg of a coating mixture identical to that of the second layer.

All the above indicated percentages are percentages by weight based on the total weight of the covering layer.

The microgranules thus obtained had a concentration of 50% by weight of lysine hydrochloride with respect to the total weight of the microgranules.

Then the microgranules were subjected to an evaluation of the degree of ruminal by-pass, post-ruminal digestibility and total bioavailability using the Boisen method. For a complete description of the Boisen method, reference is made to the publication S. Boisen, J. A. Fernàndez "Prediction of total tract digestibility of energy feedstuffs and FIG. diets by in vitro analyses" Animal Feed Science Technology 68, 277-286, 1997.

The in vitro results are highlighted in Table 5.

TABLE 5

| Sample | Content (%) | Degree of ruminal bypass (*) | Digestibility () | Bioavailability () |
| --- | --- | --- | --- | --- |
| 5 | 49.5 | 78 | 91 | 71 |

Example 3—Preparation of Microgranules Containing DL-Methionine

Example 3.1

430 kg of DL-methionine were mixed with 30 kg of rice wax spray, 25 kg of hydrogenated palm oil, 5 kg of silica, 5 kg of citric acid and 5 kg of sodium bicarbonate. The mixture was extruded using an extruder with sectors at different temperature gradients according to the following program:

| Sector 1 | Sector 2 | Sector 3 | Sector 4 | Sector 5 | Sector 6 |
| --- | --- | --- | --- | --- | --- |
| 85° C. | 45° C. | 40° C. | 40° C. | 35° C. | 60° C. |

The cores thus obtained had a concentration of 85% DL-methionine. The cores were subsequently subjected to coating in a pan.

A first coating layer was formed, coating 400 kg of microgranules with 40 kg of a coating mixture comprising:
  70% by weight of hydrogenated rapeseed oil;
  30% by weight of linolenic acid.

A second coating layer was then formed, coating the microgranules coated by the first layer with 35 kg of a coating mixture comprising:
  35% by weight of hydrogenated palm oil;
  65% by weight of carnauba wax.

A third coating layer was then formed, coating the microgranules coated by the second layer with 10 kg of a coating mixture identical to that of the first layer.

All the above indicated percentages are percentages by weight based on the total weight of the covering layer.

The microgranules thus obtained had a concentration of 70% by weight of DL-Methionine with respect to the total weight of the microgranules.

Then the microgranules were subjected to an evaluation of the degree of ruminal by-pass, post-ruminal digestibility and total bioavailability using the Boisen method. The in vitro results are highlighted in Table 6.

TABLE 6

| Sample | Content (%) | Degree of ruminal bypass (*) | Digestibility () | Bioavailability () |
|---|---|---|---|---|
| 6 | 69.3 | 82.3 | 75.0 | 61.7 |

Example 3.2

Further 400 kg of extruded granules obtained following the same procedure described in the first part of the previous example were coated in a pan using 3 coating layers.

A first coating layer was formed, coating 400 kg of microgranules with 35 kg of a coating mixture comprising:
82% by weight of hydrogenated palm oil;
18% by weight of linolenic acid.

A second coating layer was then formed, coating the microgranules coated by the first layer with 35 kg of a coating mixture comprising:
52% by weight of hydrogenated rapeseed oil;
45% by weight of carnauba wax;
3% by weight of sunflower lecithin.

A third coating layer was then formed, coating the microgranules coated by the second layer with 15 kg of a coating mixture comprising:
50% by weight of hydrogenated palm oil;
49% by weight of rice wax;
1% of ethoxylated castor oil.

All the above indicated percentages are percentages by weight based on the total weight of the covering layer.

The microgranules thus obtained had a concentration of 70% by weight of DL-Methionine with respect to the total weight of the microgranules.

Then the microgranules were subjected to an evaluation of the degree of ruminal by-pass, post-ruminal digestibility and total bioavailability using the Boisen method. The in vitro results are highlighted in Table 7.

TABLE 7

| Sample | Content (%) | Degree of ruminal bypass (*) | Digestibility () | Bioavailability () |
|---|---|---|---|---|
| 7 | 69.2 | 78.8 | 90 | 70.9 |

Example 4—Preparation of Microgranules Containing L-Lysine, Nicotinic Acid and DL-Methionine Example 4.1

180 kg of 99% choline chloride were mixed with 240 kg of 99% L-lysine hydrochloride, 65 kg of nicotinic acid (vitamin PP) and 145 kg of D, L-methionine. 20 kg of citric acid, 20 kg of sodium bicarbonate, 5 kg of sunflower lecithin and 225 kg of rice wax spray were added. The mixture was extruded.

The cores thus obtained had a concentration of 20% of choline chloride, 26.7% of L-lysine hydrochloride, 7.2% of nicotinic acid, 16.1% of D, L-methionine.

The nuclei were subjected to coating in a pan.

A first coating layer was formed, coating 400 kg of microgranules with 200 kg of a coating mixture comprising:
66% by weight of hydrogenated rapeseed oil;
34% by weight of palmitic acid.

A second coating layer was then formed, coating the microgranules coated by the first layer with 100 kg of a coating mixture comprising:
48% by weight of hydrogenated palm oil;
50% by weight of rice wax;
2% by weight of soy lecithin.

Example 5

Using the above mentioned analytical methods (pharmaceutical dissolver), in vitro tests were carried out to determine the degree of by-pass and the bioavailability of choline chloride:
a product A consisting of choline chloride, 99% pure;
a product B consisting of microencapsulated choline chloride granules obtained by means of spray-cooling technology, containing 25% by weight of choline chloride with respect to the total weight of the granule
a product C consisting of microgranules obtained according to Example 4 of the patent EP1791532, containing 50% by weight of choline chloride with respect to the total weight of the granule;
a product D consisting of microgranules obtained according to Example 1.3 described above.

Test results are shown in the following Tables 8 and 9.

Table 8 shows the results obtained considering a theoretical administration of 200 g of product.

TABLE 8

| Product | Choline Chloride administered (g) | Choline Chloride lost in the rumen in 8 h (g) | Bypassed Choline Chloride (g) | Bioavailable Choline Chloride (g) | Choline Chloride in faeces (g) |
|---|---|---|---|---|---|
| A | 198 | 198 | 0 | 0 | 0 |
| B | 50 | 37.5 | 12.5 | 12.5 | 0 |
| C | 100 | 20 | 80 | 40 | 40 |
| D | 120 | 17 | 103 | 88 | 15 |

Table 8 shows the results obtained a theoretical administration of 100 g of choline chloride.

TABLE 9

| Product | Product to be administered (g) | Choline Chloride lost in the rumen in 8 h (g) | Bypassed Choline Chloride (g) | Bioavailable Choline Chloride (g) | Choline Chloride in faeces (g) |
|---|---|---|---|---|---|
| A | 101 | 101 | 0 | 0 | 0 |
| B | 400 | 75 | 25 | 25 | 0 |
| C | 200 | 20 | 80 | 40 | 40 |
| D | 167 | 13.5 | 86.5 | 73 | 13.5 |

Example 6

Using the above mentioned analytical methods (pharmaceutical dissolver), in vitro tests were carried out to determine the degree of by-pass and the bioavailability of choline chloride:

a product A consisting of choline chloride, 99% pure;
a product B consisting of microencapsulated chlorine choline granules obtained by means of spray-cooling technology, containing 25% by weight of choline chloride with respect to the total weight of the granule
a product C consisting of microgranules obtained according to Example 4 of the patent EP1791532, containing 50% by weight of choline chloride with respect to the total weight of the granule;
a product D consisting of microgranules obtained according to Example 1.3 described above;
a product E consisting of microgranules obtained according to the extruded form of Example 1.3, but coated with coating layers devoid of pollutants;
a product F consisting of microgranules obtained according to the extruded form of Example 1.3, in which the portions of disintegrants were replaced by rice wax spray (binder), but the coating layers were "polluted" with twice the amounts of pollutant compared to Example 1.3.

The results of the tests are shown in the following Tables 10 and 11. The tables show that the mere presence of the disintegrant is effective in making the choline bioavailable in the post-ruminal phase.

Table 10 shows the results obtained considering a theoretical administration of 200 g of product.

TABLE 10

| Product | Choline Chloride administered (g) | Choline Chloride lost in the rumen in 8 h (g) | Bypassed Choline Chloride (g) | Bioavailable Choline Chloride (g) | Choline Chloride in faeces (g) |
|---|---|---|---|---|---|
| A | 198 | 198 | 0 | 0 | 0 |
| B | 50 | 37.5 | 12.5 | 12.5 | 0 |
| C | 100 | 20 | 80 | 40 | 40 |
| D | 120 | 17 | 103 | 88 | 15 |
| E | 120 | 12 | 108 | 54 | 54 |
| F | 120 | 45 | 75 | 55 | 20 |

Table 11 shows the results obtained considering a theoretical administration of 100 g of choline chloride.

TABLE 11

| Product | Product to be administered (g) | Choline Chloride lost in the rumen in 8 h (g) | Bypassed Choline Chloride (g) | Bioavailable Choline Chloride (g) | Choline Chloride in faeces (g) |
|---|---|---|---|---|---|
| A | 101 | 101 | 0 | 0 | 0 |
| B | 400 | 75 | 25 | 25 | 0 |
| C | 200 | 20 | 80 | 40 | 40 |
| D | 167 | 13.5 | 86.5 | 73 | 13.5 |
| E | 167 | 9.6 | 90.4 | 47 | 43.4 |
| F | 167 | 36.9 | 63.1 | 45.3 | 17.8 |

The invention claimed is:

1. A rumen-resistant composition in the form of microgranules, each microgranule containing:
   i) a core comprising:
      a) one or more physiologically active substances selected from the group consisting of amino acids, vitamins, enzymes, proteins, carbohydrates, probiotic microorganisms, prebiotic foods, mineral salts, choline derivatives of choline and organic acids;
      b) a matrix comprising substances selected from the group consisting of binding substances, inert substances and extrusion adjuvants; and
      c) a disintegrant agent selected from the group consisting of amides in dry form, vegetal lecithins, ethoxylated oils, monoglycerides, diglycerides of fatty acids, agar agar in dry form, effervescent mixtures of bicarbonate of an alkali metal and a polycarboxylic acid, effervescent mixtures of bicarbonate of ammonium and a polycarboxylic acid, cellulose in dry form, and methacrylate copolymers; and
   ii) at least two coating layers of the core, each having a different composition;
      wherein a first coating layer proximal to the core comprises (i) a hydrophobic substance selected from the group consisting of: fats, hydrogenated oils, monoglycerides of fatty acids, diglycerides of fatty acids, fatty acid esters, and fatty acid alcohols, and (ii) at least one pollutant substance selected from the group of emulsifying substances, fatty acids, and methacrylate copolymers;
      wherein a second coating layer, arranged on the outside of the first layer, comprises (i) at least one pollutant substance selected from the group of emulsifying substances, fatty acids, and methacrylate copolymers, and (ii) a hydrophobic substance selected from the group consisting of microcrystalline waxes, paraffin waxes, vegetal waxes and edible synthetic waxes.

2. The composition according to claim 1, wherein said emulsifying substance is selected from the group consisting of soy lecithin, sunflower lecithin, ethoxylated castor oil, alkaline metal alginates, magnesium alginates, and a combination thereof.

3. The composition according to claim 1, wherein said polluting fatty acid is selected from the group consisting of palmitic acid, oleic acid, linoleic acid, linolenic acid, stearic acid, and a combination thereof.

4. The composition according to claim 1, wherein said methacrylate copolymer is polymethyl methacrylate (PMMA).

5. The composition according to claim 1, wherein said microgranule comprises at least two coating layers; and each coating layer comprises an amount of polluting substance between 0.01% and 40% by weight with respect to the weight of the coating layer.

6. The composition according to claim 5, wherein each coating layer comprises an amount of emulsifying substance between 0.1% and 6% by weight with respect to the weight of the coating layer.

7. The composition according to claim 5, wherein each coating layer comprises an amount of polluting fatty acid between 10% and 35%.

8. The composition according to claim 1, wherein one or each coating layer comprises palmitic acid, oleic acid, linoleic acid, linolenic acid, stearic acid or a combination thereof.

9. The composition according to claim 1, wherein one or each coating layer comprises soy or sunflower lecithin.

10. The composition according to claim 1, wherein one or each coating layer comprises ethoxylated castor oil.

11. The composition according to claim 1, wherein one or each coating layer comprises sodium or magnesium alginate.

12. The composition according to claim 1, wherein one or each coating layer comprises polymethyl methacrylate (PMMA).

13. The composition according to claim 1, wherein the two coating layers comprise different amounts of pollutants.

14. The composition according to claim 1, wherein said two coating layers comprise different amounts of emulsifying substances, fatty acids, or methacrylate copolymers.

15. The composition according to claim 1,
wherein the first coating layer comprises (i) one or more hydrogenated vegetable oil in an amount that is about 50% to about 90% by weight with respect to the weight of the first coating layer, and (ii) a fatty acid and/or an emulsifying agent in an amount that is about 5% to about 50% by weight with respect to the weight of the second coating layer.

16. The composition according to claim 1, wherein in each microgranule the total weight of the coating layers is between 10% and 50% of the microgranule weight.

17. The composition according to claim 1, wherein said core comprises a disintegrant agent in an amount by weight between 1.5% and 6.5%.

18. The composition according to claim 1, wherein said core has a cylindrical shape, the height of which is comprised between 0.5 mm and 2 mm or a spheroidal shape, the diameter of which is comprised between 0.5 mm and 2 mm.

19. A premixture for animal feedstuff comprising the composition according claim 1.

20. A feedstuff comprising the premixture according to claim 19.

21. A process for the preparation of a composition according to claim 1, comprising the steps of:
obtaining microgranules by extruding a mixture comprising:
a) one or more physiologically active substances selected from the group consisting of amino acids, vitamins, enzymes, proteins, carbohydrates, probiotic microorganisms, prebiotic foods, mineral salts, choline derivatives of choline and organic acids;
b) one or more matrix substances selected from the group consisting of binding substances, inert substances, and extrusion adjuvants; and
c) a disintegrant agent selected from the group consisting of amides in dry form, vegetal lecithins, ethoxylated oils, monoglycerides, diglycerides of fatty acids, agar agar in dry form, effervescent mixtures of bicarbonate of an alkali metal and a polycarboxylic acid, effervescent mixtures of bicarbonate of ammonium and a polycarboxylic acid, cellulose in dry form, and methacrylate copolymers;
optionally subjecting the microgranule to spheronization;
forming at least two coating layers on the microgranules, each having a different composition,
wherein a first coating layer proximal to the microgranule comprises (i) a hydrophobic substance selected from the group consisting of: fats, hydrogenated oils, monoglycerides of fatty acids, diglycerides of fatty acids, fatty acid esters, and fatty acid alcohols, and (ii) at least one pollutant substance selected from the group of emulsifying substances, fatty acids, and methacrylate copolymers;
wherein a second coating layer, arranged on the outside of the first layer, comprises (i) at least one pollutant substance selected from the group of emulsifying substances, fatty acids, and methacrylate copolymers, and (ii) a hydrophobic substance selected from the group consisting of microcrystalline waxes, paraffin waxes, vegetal waxes and edible synthetic waxes.

\* \* \* \* \*